(12) United States Patent
Gozani et al.

(10) Patent No.: US 7,628,761 B2
(45) Date of Patent: Dec. 8, 2009

(54) APPARATUS AND METHOD FOR PERFORMING NERVE CONDUCTION STUDIES WITH LOCALIZATION OF EVOKED RESPONSES

(75) Inventors: Shai N. Gozani, Brookline, MA (US); Ann Pavlik Meyer, Newton, MA (US); Xuan Kong, Acton, MA (US); Martin D. Wells, Needham, MA (US)

(73) Assignee: NeuroMetrix, Inc., Waltham, MA (US)

( * ) Notice: Subject to any disclaimer, the term of this patent is extended or adjusted under 35 U.S.C. 154(b) by 0 days.

(21) Appl. No.: 10/075,217

(22) Filed: Feb. 14, 2002

(65) Prior Publication Data

US 2002/0183647 A1 Dec. 5, 2002

Related U.S. Application Data

(60) Continuation-in-part of application No. 09/625,502, filed on Jul. 26, 2000, now Pat. No. 6,379,313, which is a continuation of application No. 09/270,550, filed on Mar. 16, 1999, now Pat. No. 6,132,386, which is a continuation-in-part of application No. 09/022,990, filed on Feb. 12, 1998, now Pat. No. 5,976,094, which is a division of application No. 08/886,861, filed on Jul. 1, 1997, now Pat. No. 5,851,191.

(60) Provisional application No. 60/269,126, filed on Feb. 15, 2001.

(51) Int. Cl.
*A61B 5/05* (2006.01)
*A61B 5/00* (2006.01)
*A61B 5/04* (2006.01)

(52) U.S. Cl. .................... 600/554; 600/382; 600/383; 600/384; 600/385; 600/386; 600/387; 600/388; 600/389; 600/390; 600/391; 600/392; 600/393; 600/395; 600/546; 600/547; 600/555

(58) Field of Classification Search ......... 600/382–394, 600/547, 554, 555, 546
See application file for complete search history.

(56) References Cited

U.S. PATENT DOCUMENTS 3,572,322 A 3/1971 Wade (Continued)

FOREIGN PATENT DOCUMENTS

EP 0 025 222 A2 3/1981

(Continued)

OTHER PUBLICATIONS

Testerman, Roy, "Method of Measuring Blood Glucose Level by Sensing Evoked Action Potentials in Peripheral Nerve," Research Disclosure, 227:92, Article No. 22728, Mar. 1983.

(Continued)

*Primary Examiner*—Max Hindenburg
*Assistant Examiner*—Jeffrey G Hoekstra
(74) *Attorney, Agent, or Firm*—Pandiscio & Pandiscio (57) ABSTRACT

An apparatus and method for detecting physiological function, for example, nerve conduction, is described. In one embodiment the apparatus includes a housing including a stimulator shaped to fit a first anatomical site and a detector shaped to fit a second anatomical site. The housing automatically positions the detector substantially adjacent to the second anatomical site when the stimulator is positioned substantially adjacent to the first anatomical site. The detector contains a plurality of individual detection elements, whereby the response evoked by stimulation at the first anatomical site is measured using one or more of these detection elements at the second anatomical location.

33 Claims, 7 Drawing Sheets

U.S. PATENT DOCUMENTS

| | | | |
|---|---|---|---|
| 3,886,931 A | | 6/1975 | Rodler |
| 4,213,467 A | | 7/1980 | Stulen et al. |
| 4,583,549 A | * | 4/1986 | Manoli .................. 600/391 |
| 4,595,018 A | | 6/1986 | Rantala |
| 4,711,248 A | * | 12/1987 | Steuer et al. ............ 600/561 |
| 4,763,666 A | | 8/1988 | Strian et al. |
| 4,807,643 A | | 2/1989 | Rosier |
| 4,811,742 A | | 3/1989 | Hassel et al. |
| 5,050,612 A | | 9/1991 | Matsumura |
| 5,080,099 A | | 1/1992 | Way et al. |
| 5,092,344 A | | 3/1992 | Lee |
| 5,099,844 A | | 3/1992 | Faupel |
| 5,131,401 A | | 7/1992 | Westenskow et al. |
| 5,143,081 A | | 9/1992 | Young et al. |
| 5,203,330 A | | 4/1993 | Schaefer et al. |
| 5,215,100 A | | 6/1993 | Spitz et al. |
| 5,255,677 A | | 10/1993 | Schaefer et al. |
| 5,327,902 A | * | 7/1994 | Lemmen .................. 600/547 |
| 5,333,618 A | * | 8/1994 | Lekhtman et al. ......... 600/547 |
| 5,379,764 A | | 1/1995 | Barnes et al. |
| 5,466,256 A | | 11/1995 | McAdams et al. |
| 5,467,768 A | | 11/1995 | Suda et al. |
| 5,496,363 A | | 3/1996 | Burgio et al. |
| 5,511,553 A | | 4/1996 | Segalowitz |
| 5,540,235 A | | 7/1996 | Wilson |
| 5,560,372 A | | 10/1996 | Cory |
| 5,851,191 A | | 12/1998 | Gozani |
| 5,976,094 A | | 11/1999 | Gozani |
| 6,132,386 A | | 10/2000 | Gozani et al. |
| 6,224,549 B1 | * | 5/2001 | Drongelen .............. 600/300 |
| 6,379,313 B1 | | 4/2002 | Gozani et al. |
| 6,428,484 B1 | * | 8/2002 | Battmer et al. ........... 600/554 |
| 6,692,444 B2 | | 2/2004 | Gozani et al. |
| 2002/0123694 A1 | * | 9/2002 | Organ et al. ............ 600/547 |

FOREIGN PATENT DOCUMENTS

| | | |
|---|---|---|
| EP | 0 436 121 A1 | 7/1991 |
| EP | 0 993 270 | 4/2004 |
| JP | 1-259841 | 10/1989 |
| JP | 3-146028 | 6/1991 |
| JP | 7-308300 | 11/1995 |
| WO | WO 91/16001 | 10/1991 |
| WO | WO 92/03974 | 3/1992 |

OTHER PUBLICATIONS

Oh, Shin J., M.D., 'Clinical Electromyography: Nerve Conduction Studies,: (Williams & Wilkins, 2nd Ed., 1993).

Gilliat, R.W. and Willison, R.G., "Refractory and Supernormal Periods of the Human Median Nerve," (J. Neurol. Neurosurg. Psychiat., 2:1963) pp. 136-147.

Lindstrom, P. and Brismar, T., "Mechanism of Anoxic Conduction Block in Mammalian Nerve," (Acta Physiol Scan, 141:1991), pp. 429-433.

Basmajian, John V., M.D., and De Luce, Carlo J., Ph.D., "Muscles Alive: Their Functions Revealed by Electromyography," (Williams & Wilkins, 5th Ed., 1995).

Fujisawa, M., D.D.S. et al., "Surface Electromyographic Electrode Pair With Built-In Buffer-Amplifiers," (The Journal of Prosthetic Dentistry, vol. 63, No. 3, Mar. 1990), pp. 350-352.

Seneviratne, K.N. and Peiris, O.A., "The Effect of Ischaemia on the Excitability of Human Sensory Nerve," (J. Neurol. Neurosurg. Psychiat., 31:1968), pp. 338-347.

Shefner, Jeremy, M. M.D., "The Use of Sensory Action Potentials in the Diagnosis of Periheral Nerve Disease," (Arch-Neurol—vol. 47, Mar. 1990); pp. 341-348.

Brodie, Chaya and Sampson, S.R., "Contribution of Electrogenic Sodium-Potassium ATPase to Resting Membrane Potential of Cultured Rat Skeletal Myotubes," (Brain Research, 347:1985), pp. 28-35.

Stewart, Mark A., et al., "Substrate Changes in Peripheral Nerve During Ischemia and Wallerian Degeneration," (Journal of Neurochemistry, vol. 12, 1965), pp. 719-727.

Bostock, H. et al., "Changes in Excitability and Accomodation of Human Motor Axons Following Brief Periods of Ischaemia," (Journal of Physiology, 441:1991 Great Britain), pp. 513-535.

Nishimura, Suzushi, et al., "Clinial Application of an Active Electrode Using an Operational Amplifier," (IEEE Transactions on Biomedical Engineering, vol. 39, No. 10, Oct. 1992), pp. 1096-1099.

* cited by examiner

APPARATUS AND METHOD FOR PERFORMING NERVE CONDUCTION STUDIES WITH LOCALIZATION OF EVOKED RESPONSES

REFERENCE TO PENDING PRIOR PATENT APPLICATIONS

This application claims priority to U.S. Provisional Patent Application Ser. No. 60/269,126, filed Feb. 15, 2001, and is a continuation-in-part of U.S. patent application Ser. No. 09/625,502, filed Jul. 26, 2000 (now U.S. Pat. No. 6,379,313), which is a continuation of U.S. patent application Ser. No. 09/270,550, filed Mar. 16, 1999 (now U.S. Pat. No. 6,132,386), which is a continuation-in-part of U.S. patent application Ser. No. 09/022,990, filed Feb. 12, 1998 (now U.S. Pat. No. 5,976,094), which is a divisional application of U.S. patent application Ser. No. 08/886,861, filed Jul. 1, 1997 (now U.S. Pat. No. 5,851,191), all of which are hereby incorporated herein by reference.

FIELD OF THE INVENTION

This invention relates to apparatus and methods for the assessment of neuromuscular function. More specifically, this invention relates to apparatus and methods for diagnosing peripheral nerve and muscle diseases based on the assessment of neuromuscular function.

BACKGROUND OF THE INVENTION

Neuromuscular diseases, which represent disorders of the peripheral nerves and muscles, are a common and growing health care concern. The most prevalent neuromuscular disorders are carpal tunnel syndrome (CTS), low back pain caused by spinal root compression (i.e., radiculopathy), and diabetic neuropathy, which is nerve degeneration associated with diabetes. These conditions affect approximately thirty to forty million individuals each year in the United States alone, and have an associated economic cost greater then $100 billion annually. However, despite their extensive impact on individuals and the health care system, the detection and monitoring of such neuromuscular diseases are based on outdated and inaccurate clinical techniques or rely on expensive referrals to a specialist.

In particular, the effective prevention of neuromuscular dysfunction requires early detection and subsequent action. Even experienced physicians find it difficult to diagnose and stage the severity of neuromuscular dysfunction based on symptoms alone. The only objective way to detect many neuromuscular diseases is to measure the transmission of neural signals. The gold standard approach is a formal nerve conduction study by a clinical neurologist, but this procedure has a number of significant disadvantages. First, it requires a highly trained specialist. As a result, it is expensive and generally requires weeks or months to complete. Second, because they are not readily available, formal nerve conduction studies are generally performed late in the episode of care, thus serving a confirmatory role rather than a diagnostic one.

Thus, there is a need for making accurate and robust nerve conduction measurements available to a wide variety of health care personnel in multiple settings, including the clinic, the office, the field, and the workplace (all of which are sometimes collectively referred to as "point-of-care" settings). However, personnel in these environments generally do not have the neurophysiological and neuroanatomical training to perform such studies. In particular, the correct application of nerve conduction studies requires appropriate placement of electrodes for both stimulation of the nerve and detection of the evoked response from the corresponding nerve or muscle. Therefore, in order to provide effective nerve conduction studies in point-of-care settings, it is necessary to simplify and automate the process of correct electrode placement.

The prior art reveals a number of attempts to simplify the assessment of neuromuscular function, such as in diagnosing CTS, and to make such diagnostic measurements available to non-experts. Rosier (U.S. Pat. No. 4,807,643) describes a portable device for measuring nerve conduction velocity in patients. This instrument, however, does not provide any assistance in the correct placement of stimulation and detection electrodes. On the contrary, a skilled operator with a fairly sophisticated knowledge of nerve and muscle anatomy must ensure correct application of the device. Spitz et al. (U.S. Pat. No. 5,215,100) and Lemmen (U.S. Pat. No. 5,327,902) have also attempted to simplify nerve conduction studies. Specifically, they proposed systems that measure nerve conduction parameters between the arm or forearm and the hand, such as would be required for diagnosing CTS. Both systems suffer from several significant disadvantages, however. First, both systems are large, bulky, and constructed from rigid structures that create a supporting fixture for the arm and hand of an adult. This severely limits their portability and increases their cost. Second, these systems are only applicable to specific limbs and are not generally applicable to numerous anatomical sites. Third, these devices require highly trained operators who can make the appropriate adjustments on the apparatus so as to ensure electrode contact with the proper anatomical sites on the arm and hand. In particular, these systems provide no physiological localization of the electrodes, and as a result multiple placements are often required to find the correct electrode location.

There have been some attempts to simplify the process of nerve localization, primarily for the purpose of avoiding nerve damage during surgical procedures. For example, Raymond et al. (U.S. Pat. No. 5,775,331) describes a system for locating a nerve by applying a stimulus to a plurality of stimulation sites (such as the cavernosal nerve), recording a response to the stimulation (such as the tumescence response), and modifying the stimulation site according to an algorithm that utilizes the response. Although this invention is useful in its intended application of nerve preservation during surgery, it could not be used to simplify or automate nerve conduction studies because it does not provide means to locate the evoked response, leaving this difficult task to the operator.

The present invention avoids the aforementioned limitations.

SUMMARY OF THE INVENTION

In accordance with the present invention, an apparatus and method are provided for the substantially automated, rapid, and efficient assessment of neuromuscular function without requiring the involvement of highly trained personnel. The assessment of neuromuscular function is effected by stimulating a nerve, and then measuring the response of a muscle innervated by that nerve. The muscle response is detected by measuring the myoelectric potential generated by the muscle in response to the stimulus.

More particularly, the apparatus and method of the invention assess physiological function in, for example, the lower extremity of an individual by using an electrode to apply a stimulus to a nerve. The stimulus may be, for example, an electrical stimulus or a magnetic stimulus. Other types of stimuli may also be used. A detector, adapted for detecting the myoelectric potential generated by a muscle in response to the stimulus, detects the response of the muscle to the stimulus. An electronic controller then evaluates the physiological function of the nerve. The function is then correlated to the presence or absence of a neuromuscular pathology, such as, for example, Carpal Tunnel Syndrome (CTS) or lumbosacral radiculopathy.

In a preferred embodiment of the invention, there is provided a sensor including a stimulator electrode and a myoelectric detector. The stimulator electrode is adapted for placement at a first anatomical site substantially adjacent to a nerve, and the myoelectric detector is adapted for placement at a second anatomical site substantially adjacent to a muscle innervated by that nerve. In one embodiment, a semi-flexible connector links the stimulator electrode and myoelectric detector such that the connector automatically positions the myoelectric detector at the second anatomical site when the stimulator electrode is positioned at the first anatomical site, or vice versa.

In one embodiment, the apparatus of the invention further includes a processor for processing at least one signal detected by the myoelectric detector which is characteristic of the second anatomical site.

In a particular embodiment, the physiological function of an individual which is to be assessed by the apparatus of the invention is nerve conduction, such as conduction of the tibial nerve or the peroneal nerve. Thus, in one embodiment, the first anatomical site is a superficial location over the peroneal nerve and the second anatomical site is a superficial location over the extensor digitorum brevis muscle of the foot. Alternatively, the first anatomical site is a superficial location over the tibial nerve and the second anatomical site is a superficial location over the abductor hallucis muscle of the foot. In another embodiment, the sensor of the invention includes a positioning indicator for location over a third anatomical site such as the medial or lateral malleolus of the individual. In one embodiment the superficial location is on the skin of the individual.

In one embodiment of the apparatus of the invention, at least a portion of the body of the sensor is manufactured from a plastic, such as MYLAR. In one embodiment of the invention, the flexible connector is a strip which is rectangular, s-shaped, or any other shape configured to position the myoelectric detector over the second anatomical site when the stimulator electrode is positioned over the first anatomical site. In one embodiment, the connector includes electrical traces for carrying signals to the stimulator electrode, and from the myoelectric detector, to an electronic controller and monitor. In one embodiment, the traces connect the stimulator electrode and the myoelectric detector to the controller. In a particular embodiment of the invention, the myoelectric detector includes an electrode array that includes at least two independent interleaved bipolar recording electrodes. The signals recorded from the recording electrodes include compound muscle action potentials (CMAP's). In one embodiment, the compound muscle action potential (CMAP) is recorded over a motor point. In one embodiment of the invention, the detectable signal includes the weighted sum of the recordings of at least two of the recording electrodes.

The method of the invention relates to the assessment of physiological function using appropriate apparatus. In one form of the invention, a sensor, including a stimulator electrode and a myoelectric detector, attached by a connector, is placed on the skin of the individual overlying the anatomical location to be studied. The stimulator electrode is placed at the first anatomical site. When the stimulator electrode is positioned at the first anatomical site, the myoelectric detector is automatically positioned at the second anatomical site by the construction of the connector.

With the sensor positioned as described above on the skin of the individual, the stimulator electrode applies a stimulus to a nerve (for example, the peroneal nerve or the tibial nerve). A muscle innervated by the nerve (for example, the extensor digitorum brevis muscle of the foot with respect to the peroneal nerve, or the abductor hallucis muscle of the foot with respect to the tibial nerve) responds and thereby generates a myoelectrical potential. The signal generated by the myoelectrical potential is detected by the electrode array of the myoelectric detector and processed by the processor in communication with the myoelectric detector.

The processor processes the signals from the myoelectric detector's electrode array to select which electrode(s) of the electrode array is detecting at least one signal characteristic of the second anatomical site. The electrode selected by the processor as detecting at least one signal characteristic of the second anatomical site is used to perform nerve conduction studies to assess physiological function of the individual. The processor further processes signals from the selected electrode to perform the nerve conduction study. The processed signals are correlated to physiological function of the nerve and muscle.

The invention will be understood further upon consideration of the following drawings, description and claims. The drawings are not necessarily to scale and emphasis instead is generally being placed upon illustrating the principles of the invention.

DETAILED DESCRIPTION OF THE PREFERRED EMBODIMENTS

A primary objective of the present invention is to measure evoked potentials in peripheral nerves and muscles. The process of acquiring such measurements is commonly described as a nerve conduction study. Typical nerve conduction measurements include nerve impulse propagation latency (distal motor latency, DML, or distal sensory latency, DSL), nerve impulse velocity (conduction velocity, CV), the amplitude of the evoked neural signal (nerve action potential, NAP, amplitude), and the amplitude of the neurally evoked muscle signal (compound muscle action potential, CMAP, amplitude).

The present invention includes a nerve conduction sensor and associated algorithms. Taken together, the invention provides mechanical and electronic localization to perform accurate and reliable nerve conduction studies. Mechanical localization is a process whereby mechanical means facilitate the placement of an evoked response detector in the general vicinity of the nerve segment or muscle to be measured. Subsequently, electronic localization may be utilized to precisely investigate the electrophysiological properties of the region and identify the optimal location at which to measure the evoked response, so as to obtain accurate and reliable measurements. Through utilization of mechanical and electronic localization, the present invention obviates the need for precise electrode placement and knowledge of neuroanatomy. Instead, this knowledge is effectively encapsulated within the mechanical and electronic localization means, thereby allowing an effective nerve conduction study to be performed without requiring the involvement of highly trained personnel.

Figure 1:
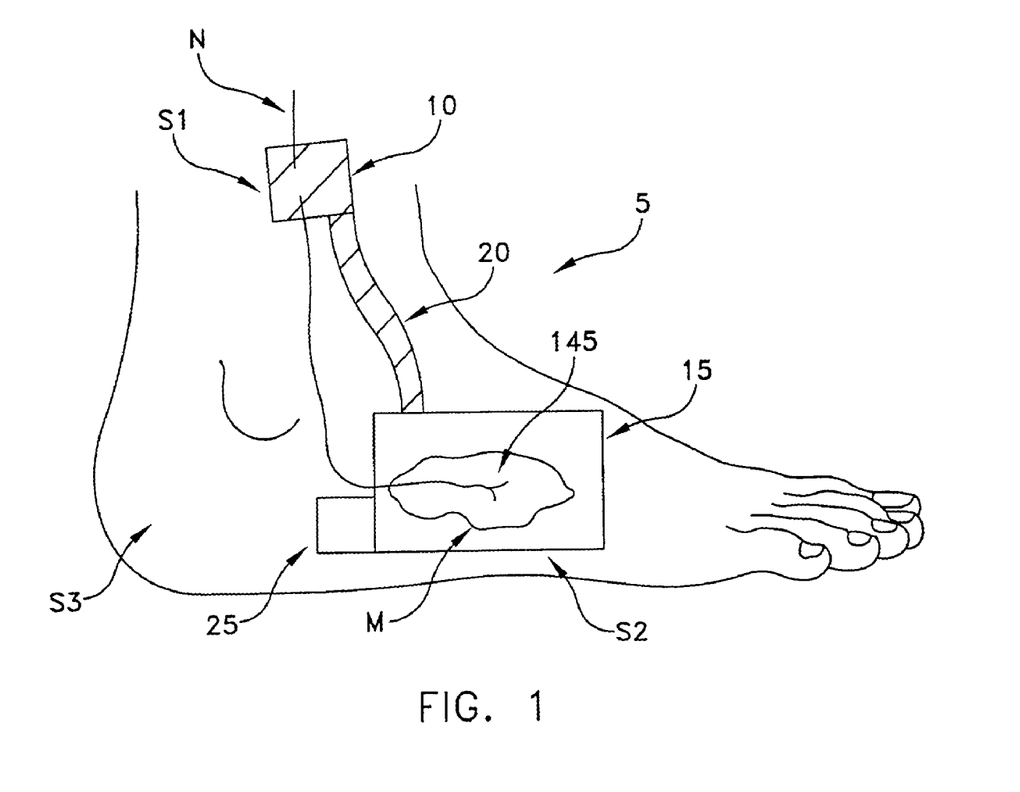
FIG. 1 illustrates one embodiment of a sensor formed in accordance with the present invention placed on the lower extremity of an individual.

In general, referring to FIG. 1, there is shown a nerve conduction sensor 5 formed in accordance with the present invention. Sensor 5 comprises a stimulator 10, a detector 15, a connector 20, and an interface 25, all integrated in a unitary housing. The stimulator 10 stimulates a peripheral nerve N at a first anatomical site S1, for example, the ankle. The detector 15 detects an evoked signal at a second anatomical site S2, which is either the nerve N stimulated by the stimulator 10 at a location different from the first anatomical site S1 or, as shown in FIG. 1, on a muscle M innervated by the stimulated nerve N, for example, the extensor digitorum brevis muscle. Other first anatomical sites S1 (for example, knee, wrist, and elbow) and other second anatomical sites S2 (for example, foot, hand, and calf) are also contemplated by the present invention and are not limited to the first and second anatomical sites illustrated in FIG. 1.

An important aspect of the present invention is the connector 20, which connects the stimulator 10 and the detector 15. The connector 20 automatically positions the detector 15 substantially adjacent to the second anatomical site S2 when the stimulator 10 is positioned at the first anatomical site S1, thus mechanically localizing the evoked signal.

Another important aspect of the present invention relates to the properties of the detector 15. In particular, the detector 15 preferably contains an element array 30 (FIG. 2) comprising a plurality of individual detection elements. The evoked response detected by the detector 15 is measured using one or more of the detection elements of the element array 30, thus electronically localizing the evoked signal.

Figure 2:
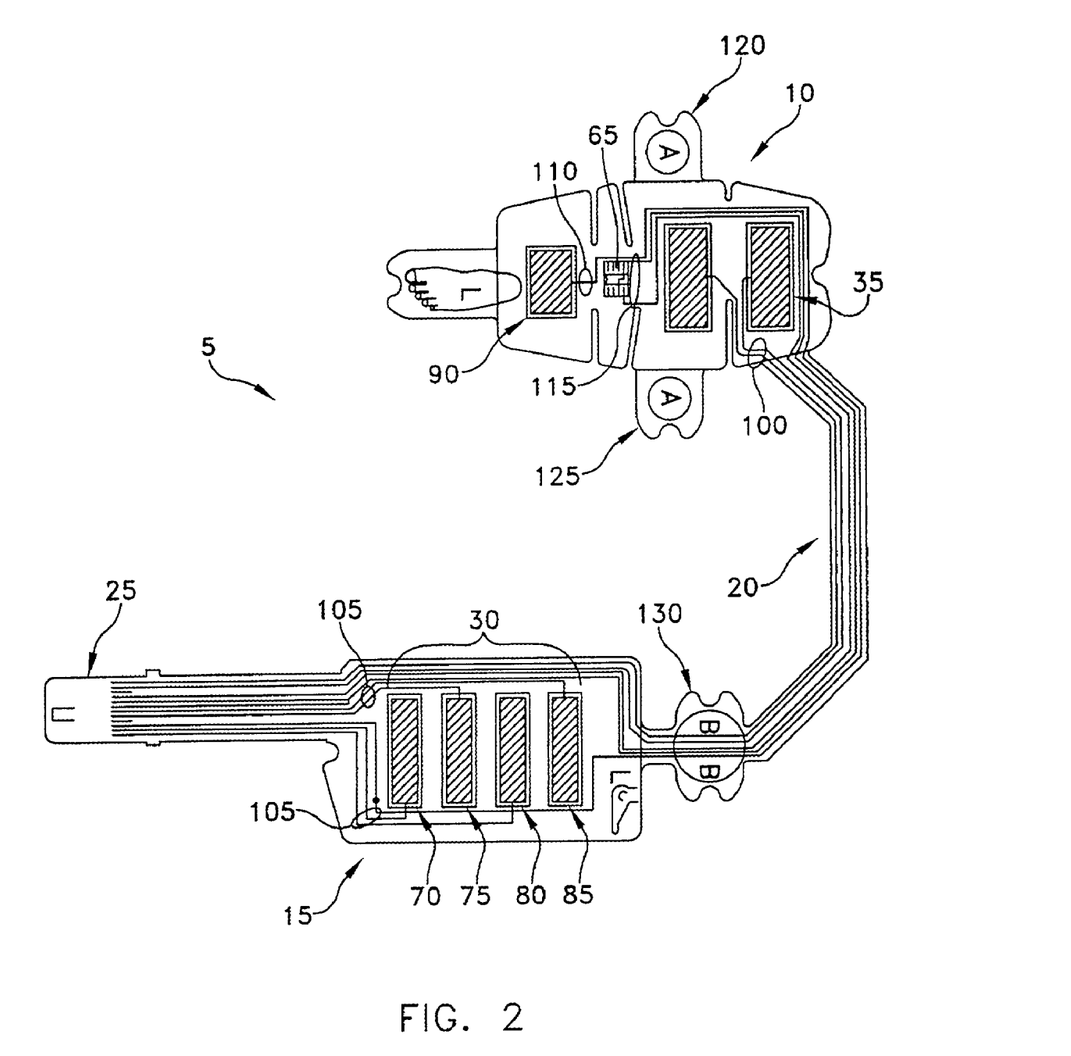
FIG. 2 illustrates one embodiment of a sensor formed in accordance with the present invention shaped to fit the foot of an individual.

FIG. 2 provides a detailed view of one embodiment of the nerve conduction sensor 5, which includes the stimulator 10, detector 15, connector 20, and interface 25. In a preferred embodiment, the nerve conduction sensor 5 is formed from multiple layers of materials. The primary base layer is preferentially formed from a continuous sheet of MYLAR. Subsequent layers include colored ink, conductive silver traces, insulating material, silver-chloride pads, hydrogel, and medical grade adhesive. The sensor is then applied to the skin of the individual so that the operative elements face inwardly, toward the patient, and so that the base layer faces outwardly, away from the patient. Details of the general construction of such layered sensors are known in the art. The connector 20 of the nerve conduction sensor 5 is configured to mechanically orient the stimulator 10 and the detector 15 relative to one another and the patient's anatomy. In particular, the connector 20 ensures that placement of stimulator 10 at a first anatomical site S1, substantially determines the orientation and position of the detector 15 at a second anatomical site S2 as illustrated in FIG. 1. In accordance with the present invention, the automatic positioning of the detector 15 need not be precise but must be substantially in the vicinity of the second anatomical site S2. The construction of connector 20 substantially limits the range of anatomic sites over which the detector 15 can be placed, so that anatomic sites that are physiologically unrelated to the stimulation site S1 (e.g., anatomical site S3 in FIG. 1.) are not accessible to the detector 15.

In a preferred embodiment, the connector 20 is formed from MYLAR. However, other materials such as various plastics may also be used. The particular connector configuration shown in FIG. 2 is intended to be illustrative and other configurations may also be used and should be considered to be within the scope of the present invention. For example, in another embodiment, the stimulator 10 and the detector 15 are contiguous and attached. The construction of connector 20 is limited only by the objective that placement of the stimulator 10 at the first anatomical site S1 automatically places the detector 15 substantially adjacent to the second anatomical site S2. The converse will also hold, i.e., placement of the detector 15 at the second anatomical site S2 automatically places the stimulator 10 at the first anatomical site S1.

Figure 2A:
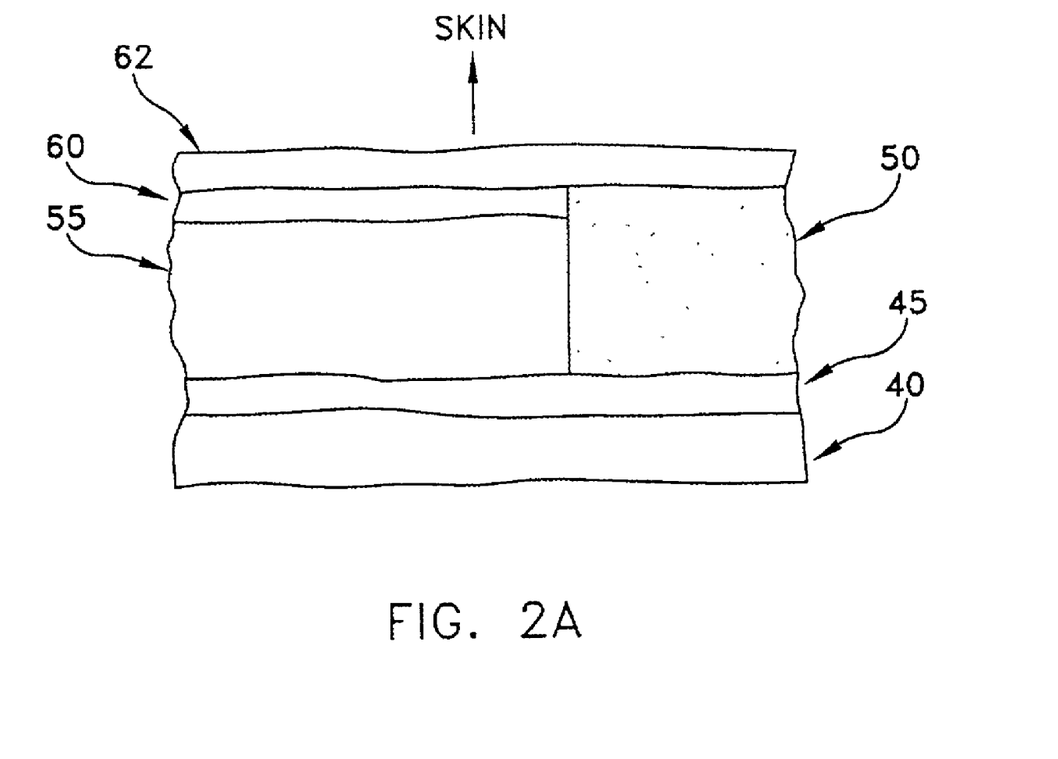
FIG. 2A is a cross-sectional view illustrating one way of fabricating the sensor of the present invention.

The stimulator 10 includes at least one stimulation element 35 (FIG. 2) that delivers a stimulus to a peripheral nerve. The stimulus can be electrical, magnetic, optical, chemical, or biological. In a preferred embodiment, the stimulus is an electrical impulse and the stimulation element 35 includes a plurality of layers of different materials which together form the stimulation electrode. By way of example, and looking at FIG. 2A, stimulation electrode 35 may include a mylar substrate 40, a layer of conductive ink 45, a conductive gel 50 bordered by a foam mask 55, a layer of adhesive 60, and a release liner 62.

In a preferred embodiment of the invention illustrated in FIG. 2, the stimulator 10 includes a temperature probe 65. When the stimulator 10 is placed on the individual, the temperature probe comes into contact with the test subject's skin and measures the skin surface temperature. This temperature is then used for calibrating the system. Other locations for the temperature probe 65 have been contemplated and include sites within the detector 15 and the connector 20.

Referring still to FIG. 2, in one embodiment of the invention, the detector 15 includes an array 30 of detection elements. The detection elements may be capable of detecting bioelectrical, magnetic, optical, chemical or biological signals. In a preferred embodiment, bioelectrical signals, and more specifically biopotentials, are detected, and the array 30 includes at least four electrodes 70, 75, 80 and 85 (collectively, the array 30), preferably arranged in a linear configuration such as shown in FIG. 2. However, other configurations, such as a matrix of electrodes, and different numbers of electrodes, have been contemplated and should be considered within the scope of the present invention.

The detector array 30 illustrated, for example, in FIG. 2 allows the detector 15 to adapt to variations in the anatomic location, physical structure and physiological organization of the second anatomical site S2, such as a muscle M. In a preferred embodiment, the electrodes 70, 75, 80 and 85 are composed of a plurality of layers of different materials with substantially the same area. Again, a construction such as that shown in FIG. 2A may be used. In many applications, such as in the recording of electrical signals, a distinct reference electrode is required. This reference electrode essentially establishes a "zero point" that other voltages may be referenced against. Such a reference electrode 90 is shown in FIG. 2. In this embodiment, the reference electrode 90 provides a reference voltage for acquisition of biopotentials signals from detector array 30 of the detector 15. In one embodiment, shown in FIG. 2, the reference electrode 90 is located on the stimulator 10. In other embodiments, the reference electrode 90 is located on the detector 15, on the connector 20, or on another part of the nerve conduction sensor 5.

The stimulator electrode 10 and the bioelectrical detector 15 are formed in the nerve conduction sensor 5 so as to make contact with the skin of the individual when the nerve conduction sensor 5 is in position on the individual. In one embodiment, the nerve conduction sensor 5 may be configured for different sizes (e.g., small, medium and large), for different nerves (e.g., median, ulnar, peroneal, and posterior tibial nerves), for different muscles (e.g., extensor digitorum brevis, adductor hallucis brevis), for right and left anatomical sites, and for various anatomical sites (e.g., ankle, foot, hand, wrist).

Figure 3:
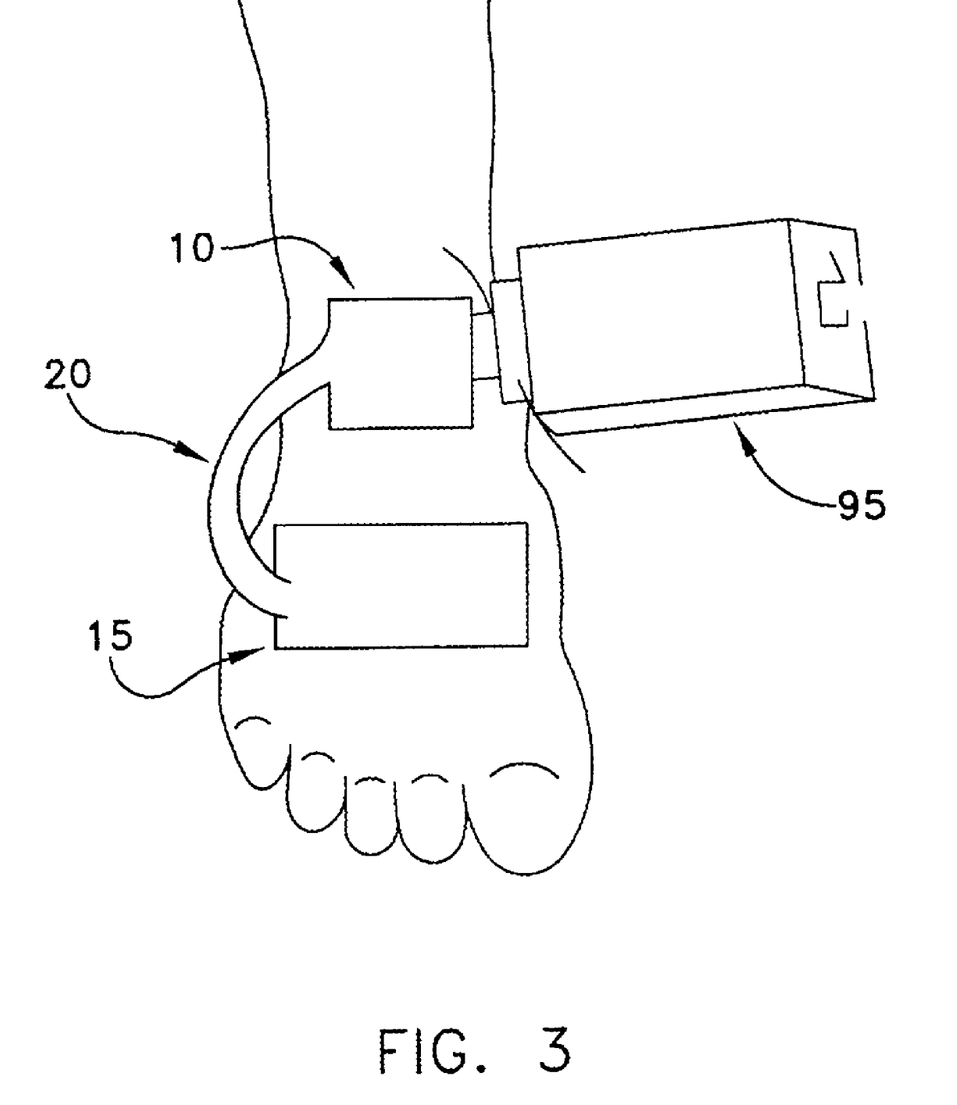
FIG. 3 illustrates the embodiment of FIG. 2 positioned on the foot of a patient.

Referring to FIG. 2, in one embodiment, the nerve conduction sensor 5 has an interface 25 that serves as a communications port between the nerve conduction sensor 5 and external devices, such as an electronic controller 95 (see FIG. 3). The nerve conduction sensor 5 also has a series of traces that provide communication between the interface 25 and internal elements of the sensor. In a preferred embodiment, illustrated in FIG. 2, these traces 100, 105, 110 and 115 are capable of transmitting electronic signals and are embedded within a unitary housing of sensor 5. As shown in FIG. 2, the nerve conduction sensor 5 includes traces 100 that communicate signals from the stimulation elements 35 on the stimulator 10 to the interface 25; traces 105 that communicate signals from the element array 30 on the detector 15 to the interface 25; traces 110 that communicate signals from the reference electrode 90 to the interface 25; and traces 115 that communicate electronic signals from the temperature probe 65 to the interface 25. In one embodiment, the traces are created by printing silver lines 45 (FIG. 2A) on the Mylar substrate 40 which are in direct communication with conductive gels 50 at both the stimulation and detection sites. In this embodiment, the foam mask 55 is positioned on top of these traces to prevent shorting.

Referring still to FIG. 2, in one embodiment, the nerve conduction sensor 5 includes indicators 120 and 125 to aid in positioning the sensor on the individual's extremity. In a preferred embodiment, the nerve conduction sensor 5 includes positioning indicators 120 and 125 to help place the stimulator 10 correctly; connector 20 then ensures that detector 15 is positioned appropriately. In another embodiment, another positioning indicator 130 helps place the detector 15 correctly; connector 20 then ensures that stimulator 10 is positioned appropriately. In yet another embodiment, indicators 120, 125 and 130 are all provided on a sensor 5.

According to a method of the invention, the positioning indicators 120, 125 and 130 are placed on the skin of the individual at particular anatomical sites, thereby aiding in the placement and orientation of the nerve conduction sensor 5 on the extremity of the individual. The positioning indicators 120, 125 and 130, shown in FIG. 2, are merely illustrative and other embodiments with various positioning indicators and mechanisms known to the skilled person are contemplated by the invention.

As illustrated in FIG. 3, the nerve conduction sensor 5 is interfaced to an electronic controller 95. The electronic controller 95 includes a generator to generate electrical stimuli that stimulate the nerve N through the stimulator 10, a signal detector to detect signals from a nerve N or muscle M (evoked by stimulation by the stimulator 10) through the detector 15, a processor to process the detected signals, and a display to communicate the results to an operator or another electronic device such as a computer. In one embodiment, the electronic controller 95 includes a controller detector to detect the evoked response from detector 15 and a transmitter to transmit this information to a remote processor for further processing and analysis. This transmitter may be telephone lines, the Internet, or wireless networks. In another embodiment, the electronic controller 95 includes an amplifier to amplify, a recorder to record, and a processor to process bioelectrical signals generated by detector 15.

One embodiment of the controller 95 contains two differential amplifiers each of which is connected to two electrodes within the electrode array 30. In one particular embodiment, one differential amplifier is electronically connected to electrodes 70 and 80, through interface 25 and traces 105, and another differential amplifier is electronically connected to electrodes 75 and 85, through interface 25 and traces 105. This configuration thus represents two differential bipolar recordings. Other configurations by which the electrodes 30 are connected to the amplifier have been contemplated and should be considered within the scope of the present invention.

In another aspect, the invention is a method for performing nerve conduction studies. As an illustrative example, motor nerve conduction studies may be performed with the nerve conduction sensor 5. This is accomplished by placing the stimulator electrode 10 of the sensor 5 over the nerve N to be studied, for example the peroneal nerve at the ankle. The connector 20 of the sensor 5 then automatically places the detector 15 substantially adjacent to a muscle M innervated by the nerve N, for example the extensor digitorum brevis muscle on the lateral aspect of the mid foot. After the detector 15 is put in contact with the individual's skin, one or more of the detection electrodes in array 30 are selected, preferably according to an algorithm described below and illustrated in FIG. 5. Subsequently, myoelectrical activity is recorded from the muscle M in response to stimulation of the nerve N by the stimulator 10. The motor nerve conduction study is thus carried out by repeatedly stimulating the nerve N and recording the resulting evoked responses by the chosen detection electrodes in array 30. The evoked response thus detected provides information on the function of the nerve and muscle and may include the distal motor latency (DML), the compound action potential (CMAP) amplitude, the F-wave latency, the F-wave amplitude, the refractory period, the activity dependence, the stimulation threshold, and other nerve conduction parameters familiar to those knowledgeable in the art. The particular detection electrodes in array 30 do not need to be constant throughout the nerve conduction study. In other words, some of the detection electrodes can be used in one part of the study, and other electrodes can be used in a different part of the study.

Figure 4:
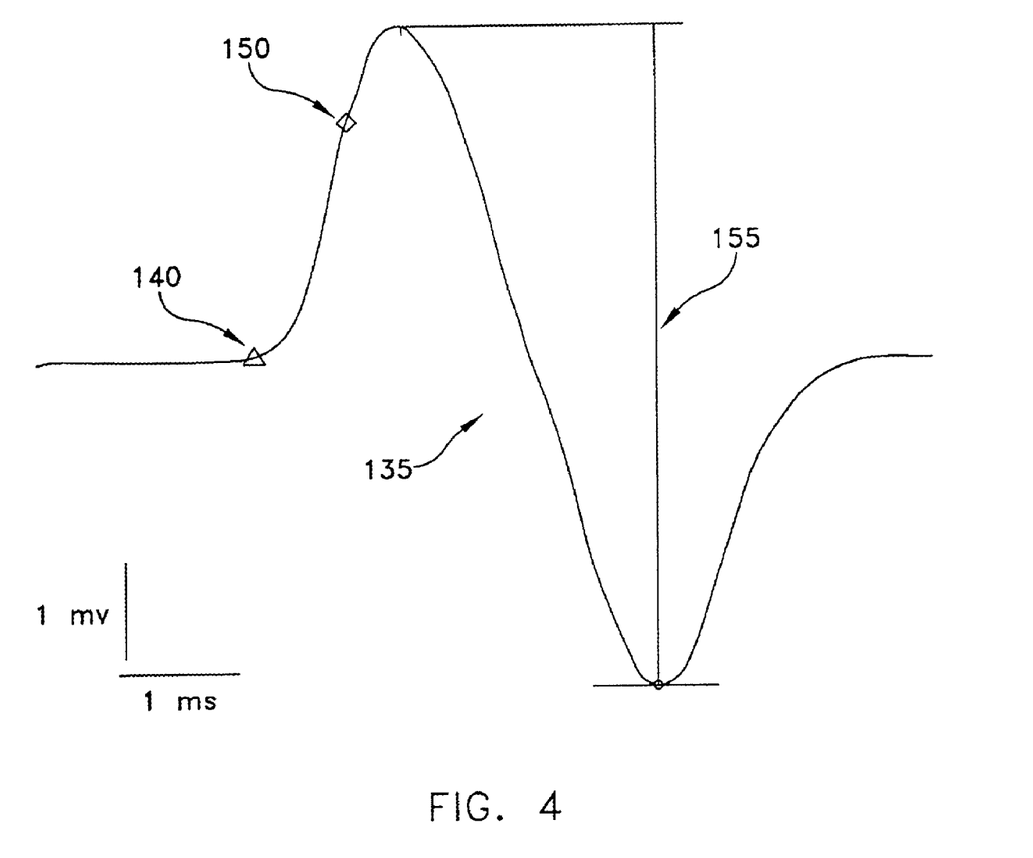
FIG. 4 is a graph in the time domain of the muscle response evoked and measured by an embodiment of the present invention.

In a preferred embodiment of the invention, the electronic controller 95 (FIG. 3) and the nerve conduction sensor 5 are configured so that the electronic controller acquires two signals formed from two interleaved pairs of detection electrodes in array 30. Signals thus recorded are called bipolar signals. An embodiment of a bipolar signal 135 is illustrated in FIG. 4. The signal 135 has a number of features that are important both for the assessment of nerve conduction parameters, such as those described above, as well as for the determination of the anatomical and physiological relationship between the detection electrodes and the underlying muscle M. One feature is the latency 140 of the signal. The latency 140 represents the time between the stimulation of nerve N and arrival of the impulse at the innervated muscle M. Latency 140, and its associated parameter velocity, are generally considered to be the most important nerve conduction parameters. In this respect it should be appreciated that diseased nerves have a longer latency than normal nerves. In addition, the specific electrode located closest to the muscle motor point 145 (FIG. 1) will typically have the lowest latency among the electrode array 30.

Another feature of the signal 135 is the maximum rising slope 150 of the signal. This parameter represents the depolarization of the muscle tissue M. The maximum rising slope 150 is particularly important because the signal recorded over the motor point 145 (FIG. 1) generally has a larger slope 150 than a biopotential recorded away from the motor point 145.

Another feature of the signal 135 is the peak-to-peak amplitude 155 of the signal 135. This parameter represents the overall size of the muscle action potential. This is an important characteristic, inasmuch as diseased nerves typically have a lower amplitude 155 than healthy nerves. In addition, signals 135 recorded over the motor point 145 generally have larger peak-to-peak amplitude 155 than those recorded away from the motor point 145.

The aforementioned features of signal 135 should only be considered to be representative of those used to determine nerve conduction and muscle structure. Other features have been contemplated and should be considered within the scope of the present invention.

As mentioned above, the performance of nerve conduction studies with the nerve conduction sensor 5 requires selection of one or more electrodes from array 30 from which the evoked response is measured and nerve conduction parameters, such as the distal motor latency, are determined. In the illustrative example of a motor nerve conduction study, the evoked response must be recorded from the motor point— which is the region of the muscle innervated by the nerve. The objective of the electrode array 30 is to provide means for sampling the evoked response from all or a section of the muscle, and to determine the single electrode or combination of electrodes that best represent the evoked response from the motor point. In the most general case, the evoked response is a weighted sum of one or more electrodes. However, in a preferred embodiment, the single electrode that best represents the motor point response is used.

Figure 5:
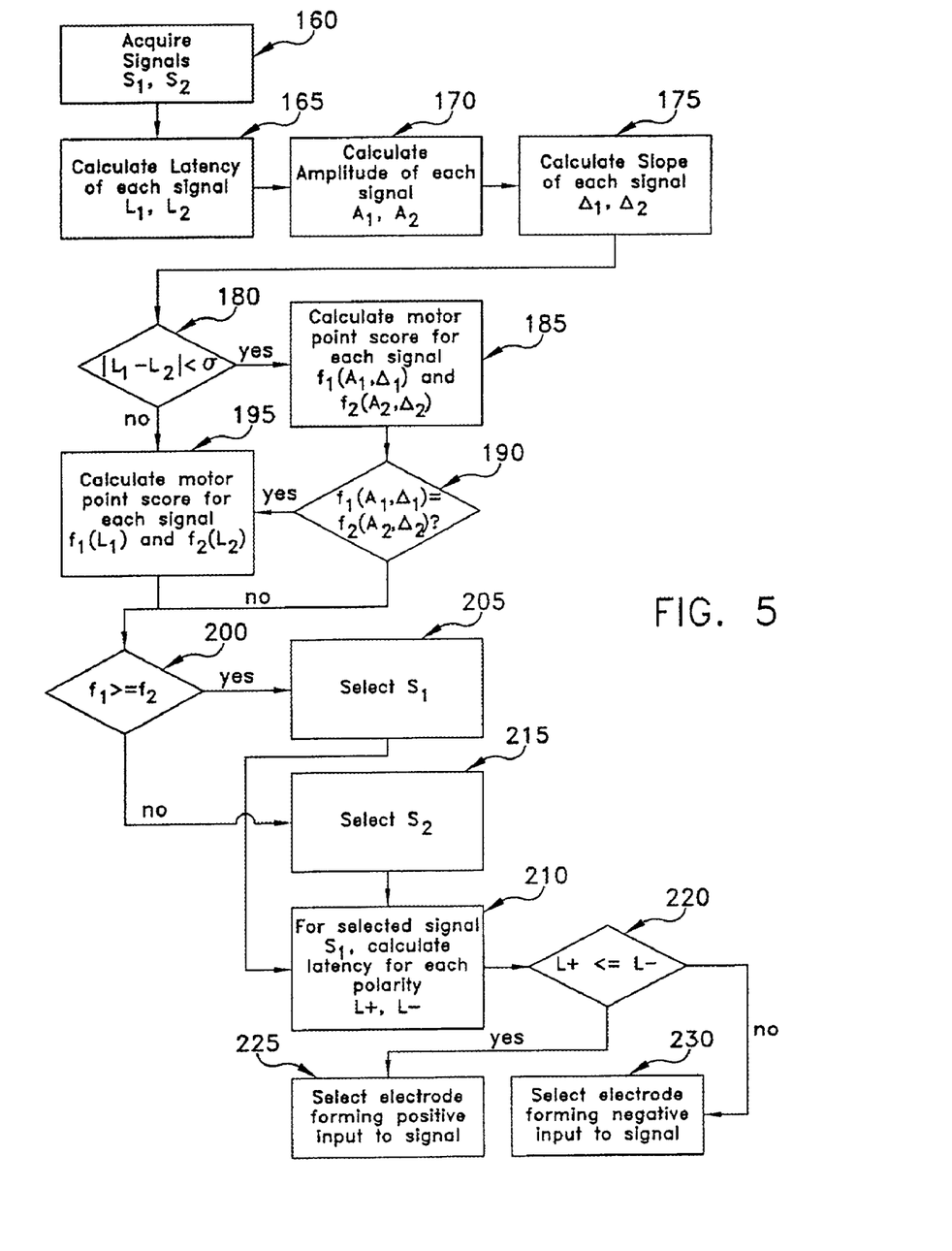
FIG. 5 is a flowchart illustrating the steps in one embodiment of the invention to select optimum recording electrode pairs.

FIG. 5 illustrates a preferred algorithm for utilizing the signals 135 recorded from the electrode array 30 to select the optimal electrode(s) 70, 75, 80, 85 for performance of nerve conduction studies. In process step 160, two signals $S_1$ and $S_2$ are acquired. In a preferred embodiment, these signals are differentially recorded from two interleaved pairs of electrodes 70, 80, and 75, 85 and typically have a waveform shape and feature set similar to those shown, for example, in FIG. 4. In this embodiment, $S_1 = V(E_{70}) - V(E_{80})$ and $S_2 = V(E_{75}) - V(E_{85})$, where $V(E_X)$ is the biopotential at electrode $E_X$, and $E_{70}$ and $E_{75}$ form the positive differential inputs and $E_{80}$ and $E_{85}$ form the negative differential inputs of their respective signals. These signals are only illustrative and embodiments have been contemplated in which different combinations of electrodes are utilized, such as 70, 75, and 80, 85, or 70, 85, and 75, 80, in which each of the electrodes is recorded relative to a common indifferent electrode, and in which the electronic controller 95 has means to dynamically create various combinations of differential recordings. In addition, although the illustrative algorithm is described in terms of two signals, it can be applied to a greater number of signals formed from recordings of the electrode array 30.

According to one embodiment of the invention, predetermined signal features (latency, amplitude and slope, respectively) are calculated for each of the two signals $S_1$ and $S_2$ in process steps 165, 170 and 175. In a preferred embodiment, these parameters are independent of the optimal polarity of the signals. In other words, the same parameters are calculated for $S_i$ and $-S_i$. Furthermore, these parameters are illustrative and additional parameters may be used. After calculation of the signal features, the algorithm continues with process step 180, in which the latencies ($L_1$ and $L_2$) of the two signals are compared to determine if they are within a predetermined range, σ, of one another. In a preferred embodiment, the predetermined range is between about 0.1 and 0.7 ms, preferably 0.4 ms. If the latency difference is within the predetermined value, then the algorithm continues with process step 185. In this step, a score ($f_1$ and $f_2$) is determined for each signal from the non-latency parameters by creating a linearly weighted sum of these parameters using predetermined coefficients. Subsequently, in process step 190, the scores are compared for equality. If they are equal then the algorithm continues with process step 195. If they are not equal then the algorithm continues with process step 200. If the latency difference is not within the predetermined range as determined in step 180, then the algorithm continues with process step 195. In step 195, a score is determined for each signal based entirely on its corresponding latency. In a preferred embodiment, this score is inversely proportional to the latency such that a shorter latency will yield a higher score. As an example, the following scoring function has been contemplated.

$$f_i = \frac{1}{L_i}$$

Upon completing the score calculation in process step 195, the algorithm continues with process step 200 in which the scores for the two signals ($f_1$ and $f_2$, regardless of whether calculated in process step 185 or 195) are compared. If the first signal has a greater or equal score to the second signal, then the algorithm continues with process step 205 in which the first signal is chosen for subsequent processing and then the algorithm proceeds to process step 210. If in process step 200, the first signal has a lower score than the second signal, then the algorithm proceeds to process step 215 in which the second signal is chosen for subsequent processing before continuing with process step 210.

In process step 210 the latency of the chosen signal ($S_1$ if from process step 205 and $S_2$ if from process step 215) is calculated for each polarity yielding two latencies, $L_+$ and $L_-$. The algorithm then proceeds to process step 220 where the latencies are compared. If the positive polarity latency ($L_+$) is less than or equal to the negative polarity latency ($L_-$), then the algorithm proceeds to process step 225 where the optimal recording electrode is reported as the positive input to the differential recording. For example, in the embodiment in which the first signal is formed from a differential recording of electrodes 70 and 80, the reported electrode would be electrode 70. If in process step 220, the negative polarity latency ($L_-$) is less than the positive polarity latency ($L_+$), then the algorithm proceeds to process step 230 where the optimal recording electrode is reported as the negative input to the differential recording. For example, in the embodiment in which the first signal is formed from a differential recording of electrodes 70 and 80, the reported electrode would be electrode 80.

In the preferred algorithm shown in FIG. 5, a set of predetermined linear weights is utilized in process step 185 to generate a score indicating which signal is optimal. In the preferred embodiment, these weights are obtained by performing a linear regression between an ensemble of signals and an expert's assessment of their optimality. As an illustrative example, a set of signals is obtained with the nerve conduction sensor and then a neurophysiological expert assigns an optimality score to them. Subsequently, the scoring function is calculated by performing a linear regression between the signals and the expert score. In one embodiment, the expert score indicates whether the electrodes from which the signal was obtained are over the muscle motor point. Although the scoring function in the illustrative algorithm is linear, it may also be non-linear. For example, in another embodiment, the scoring function is determined by logistic regression analysis. In yet another embodiment, the scoring function is neural network trained by a technique such as backwards propagation. In yet another embodiment, a combination of fuzzy logic and expert system based technique can be used to derive the scoring function.

Figure 6:
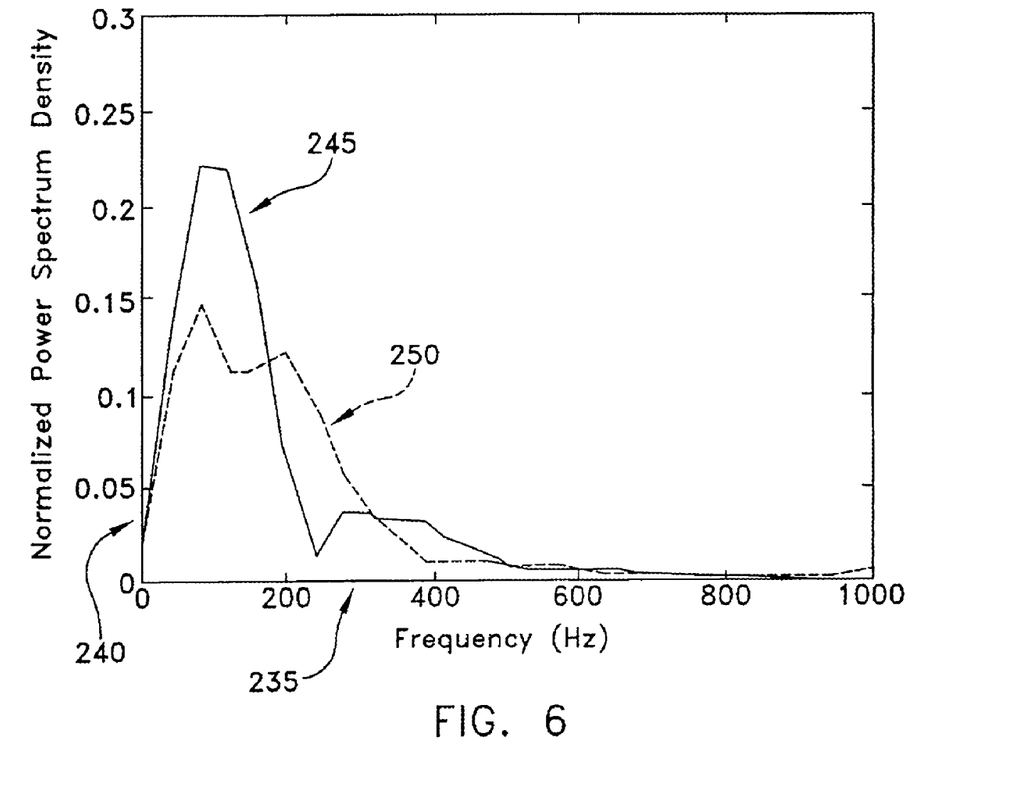
FIG. 6 is a graph in the frequency domain showing the power spectral density of muscle responses evoked and measured by one embodiment of the invention.

In the illustrative algorithm of FIG. 5, time domain features of the recorded signal are utilized to determine the optimal electrode. However, frequency based analysis has also been contemplated, either independently or in conjunction with above time-domain analysis. FIG. 6 shows the power spectrum of two bipoloar signals recorded with the nerve conduction sensor 5. The horizontal axis 235 shows frequency. The vertical axis 240 shows the power spectral density, which was calculated by taking the discrete Fourier transform of each signal and then normalizing the spectral energy to the maximum value. This allows the resulting power spectral densities 245 and 250 to be compared. A signal recorded over the motor point 145 will have a simpler morphology than one recorded away from the motor point 145. As a result, the signal recorded from the motor point 145 can be determined by that which concentrates more towards lower frequencies. In the illustrative example shown in FIG. 6, signal 245 has proportionally more energy at lower frequencies than does signal 250. Thus, signal 245 is expected to be closer to the motor point 145. Features derived from other transformations such as wavelet and multi-resolution analysis can also be used to determine motor point.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

What is claimed is:

1. A method for assessing physiological function in an individual, comprising:
   (a) placing a sensor superficially on an individual, said sensor comprising a stimulator, a detector, and a flexible connector formed integral with and serving as a mechanical and electrical connection between said stimulator and said detector:
   said stimulator being shaped to fit a first anatomical site and configured to generate a stimulus and apply said stimulus to stimulate a nerve at said first anatomical site;
   said detector being shaped to fit a second anatomical site, said detector comprising a plurality of electrodes each configured to detect a response signal generated at said second anatomical site in response to said stimulus, said detector being made so that said electrodes have fixed positions proximate one another; and
   said connector being configured to mechanically orient said stimulator and said detector relative to one another and automatically position said detector substantially adjacent to said second anatomical site when said stimulator is placed substantially adjacent to said first anatomical site on the surface of an individual, whereby said electrodes are located at proximate points along said surface; and
   (b) performing nerve conduction studies with at least one of said electrodes to assess physiological function in an individual;
   wherein said nerve conduction studies comprises:
   (c) operating said stimulator to stimulate said first anatomical site and monitoring said plurality of electrodes to detect response signals produced at said second anatomical site in response to the stimulation at said first anatomical site;
   (d) processing the response signals detected by said electrodes, said processing involving an evaluation of selected parameters of each of said response signals and a comparison of said response signals according to the evaluated selected parameters;
   (e) selecting on the basis of said comparison of said response signals processed in step (d) at least one electrode detecting a response signal characteristic of said second anatomical site; and
   (f) performing said nerve conduction studies according to step (c) with said at least one electrode selected in step (e).

2. The method of claim 1 wherein in step (f) said nerve conduction studies comprise measurement of an F-wave latency.

3. The method of claim 1 wherein in step (f) said nerve conduction studies comprise measurement of a motor latency.

4. The method of claim 1 wherein in step (f) said nerve conduction studies comprise measurement of a sensory latency.

5. The method of claim 1 wherein in step (f) said nerve conduction studies comprise measurement of a sensory amplitude.

6. The method of claim 1 wherein in step (d) said processing comprises amplitude comparison between a plurality of response signals generated at said second anatomical site.

7. The method of claim 6 wherein in step (d) said amplitude comparison comprises maximal peak to peak amplitude.

8. The method of claim 1 wherein in step (d) said processing comprises frequency spectrum comparison between a plurality of response signals generated at said second anatomical site.

9. The method of claim 8 wherein said frequency spectrum comparison comprises discrete Fourier transform analysis of said plurality of response signals generated at said second anatomical site and comparison of the spectral components of said plurality of response signals.

10. The method of claim 9 wherein in step (d) said at least one electrode detects response signals that have more energy at low frequencies.

11. The method of claim 1 wherein at least one response signal generated at said second anatomical site comprises peripheral evoked potentials.

12. The method of claim 1 wherein the nerve conduction studies of step (f) involve detecting at least one signal generated at said second anatomical site comprising compound muscle action potential.

13. The method of claim 1 wherein said at least one electrode selected in step (d) is located over a muscle motor point at said second anatomical site.

14. The method of claim 1 wherein said first site is a location over a nerve and said second site is a location over a muscle innervated by said nerve or a location over different portion of said nerve.

15. A method for assessing physiological function in an individual, comprising:
   (a) providing a sensor for superficial application to an individual, said sensor comprising:
      a stimulator for generating a nerve stimulus, said stimulator being shaped to fit a first anatomical site whereby application of said stimulus stimulates a nerve at said first anatomical site; and
      a detector shaped to fit a second anatomical site, said detector comprising a plurality of electrodes each capable of detecting a signal generated at said second anatomical site in response to said stimulus applied at said first anatomical site, with said electrodes being fixed in spaced relation with one another, and
      a flexible connector connecting said stimulator to said detector to form an integral unitary structure;
      said flexible connector being constructed and shaped to effect mechanical localization of said detector relative to said stimulator whereby said detector will be automatically positioned substantially adjacent to said second anatomical site when said stimulator is placed substantially adjacent said first anatomical site on the surface of an individual;
   (b) placing said sensor superficially on an individual so that said stimulator is located at and fits said first anatomical site and said detector is located at and fits said second anatomical site; and
   (c) performing nerve conduction studies with said sensor to assess physiological function in an individual, said studies comprising (1) causing said stimulator to generate a stimulus on said individual at said first anatomical site, (2) causing said electrodes of said detector to detect response signals generated at said second anatomical site in response to said stimulus applied at said first anatomical site, and (3) recovering said response signals;
   (d) processing the recovered response signals generated at said second anatomical site and detected by said electrodes to effect selection of at least one electrode detecting a response signal characteristic of said second anatomical site, said selection involving evaluating two or more selected parameters of said response signals and comparing said response signals according to said evaluated selected parameters; and
   (e) performing the additional nerve conduction studies specified in step (c) with the at least one electrode selected in step (d).

16. The method of claim 15 wherein in step (d) said processing comprises amplitude comparison between a plurality of response signals generated at said second anatomical site.

17. The method of claim 16 wherein said amplitude comparison comprises maximal peak to peak amplitude.

18. The method of claim 15 wherein in step (d) said processing comprises frequency spectrum comparison between a plurality of response signals generated at said second anatomical site.

19. The method of claim 18 wherein said frequency spectrum comparison comprises discrete Fourier transform analysis of said plurality of response signals generated at said second anatomical site and comparison of the spectral components of said response signals.

20. The method of claim 19 wherein the at least one electrode selected in step (d) is selected because the response signals detected by said at least one electrode has more energy at low frequencies.

21. The method of claim 15 wherein each of said response signals generated at said second anatomical site comprises peripheral evoked potentials.

22. A method for assessing physiological function in an individual, comprising:
   (a) providing a sensor comprising a stimulator, a detector, and a flexible connector formed integral with and serving as a mechanical and electrical connection between said stimulator and said detector:
      said stimulator being shaped to fit a first anatomical site and configured to generate an electrical stimulus to stimulate a nerve at said first anatomical site;
      said detector being shaped to fit a second anatomical site, said detector comprising a plurality of electrodes each configured to detect response signals evoked by a muscle at said second anatomical site in response to said stimulus, said electrodes being in fixed spatial relation to one another; and
      said connector being constructed so as to determine the spatial position of said detector relative to said stimulator and being configured to automatically position said detector substantially adjacent to said second anatomical site when said stimulator is placed substantially adjacent to said first anatomical site on the surface of an individual; and
   (b) placing said sensor on an individual so that said stimulator is positioned substantially adjacent to a first anatomical site characterized by a nerve to be studied and said detector is positioned adjacent to a second anatomical site characterized by a muscle associated with said nerve,
   (c) operating said stimulator to stimulate said nerve at said first anatomical site;
   (d) operating said detector so as to cause said electrodes to detect response signals evoked by said muscle at said second anatomical site in response to the stimulation of said nerve at said first anatomical site;
   (e) processing the response signals detected by said electrodes to determine from parameters of said response signals the electrode or electrodes located closest to the motor point of said muscle; and
   (f) with said sensor still in place on said individual, performing nerve conduction studies using the detector electrode(s) located closest to the motor point of said muscle.

23. The method of claim 22 wherein said response signals are in the form of biopotentials detected on the skin of said individual overlying said second anatomical site.

24. The method of claim 22 wherein step (e) involves determining the latency, peak-to-peak amplitude and slope of said response signals and determining therefrom the detector electrode(s) located closest to the muscle point of said muscle.

25. The method of claim 22 wherein the nerve conduction studies performed according to step (f) comprise measurement of an F-wave latency.

26. The method of claim 22 wherein the nerve conduction studies performed according to step (f) comprise measurement of a motor latency.

27. The method of claim 22 wherein the nerve conduction studies performed according to step (f) comprise measurement of compound muscle action potential.

28. The method of claim 22 wherein the processing of step (e) comprises amplitude comparison between a plurality of response signals generated at said second anatomical site.

29. The method of claim 22 wherein said processing of step (e) comprises frequency spectrum comparison between a plurality of response signals generated at said second anatomical site.

30. The method of claim 22 wherein the nerve conduction studies performed according to step (f) are conducted by (1) causing said stimulator to generate a stimulus on said individual at said first anatomical site, (2) causing said selected electrodes of said detector to detect response signals generated at said second anatomical site in response to said stimulus applied at said first anatomical site, and (3) evaluating said response signals detected by said selected electrodes by measuring one or more of the following parameters: F-wave latency, F-wave amplitude, distal motor latency (DML), compound action potential (CMAP) amplitude, refractory period, activity dependence, and stimulation threshold.

31. The method of claim 22 wherein the determination of the electrode or electrodes located closest to the muscle point of said muscle according to step (e) is accomplished by means of an algorithm that involves evaluation of several selected parameters of the response signals detected by said plurality of electrodes.

32. A method for conducting nerve conduction studies of a nerve segment or muscle in an individual, said method comprising:
(a) providing a sensor adapted for application superficially on an individual, said sensor comprising a stimulator, a detector, and a flexible connector formed integral with and serving as a mechanical and electrical connection between said stimulator and said detector, with said stimulator, detector and connector having a common substrate whereby they form an integral unit:
said stimulator being shaped to fit a first anatomical site constituting a first superficial location over a nerve of an individual and configured to generate a stimulus and apply said stimulus to stimulate said nerve;
said detector being shaped to fit a second anatomical site constituting a second superficial location over a muscle innervated by said nerve or a segment of that nerve, said detector comprising a plurality of electrodes each configured to detect a response signal generated at said second anatomical site in response to said stimulus, said detector being made so that said electrodes have fixed positions proximate one another; and
said connector being configured to mechanically orient said stimulator and said detector relative to one another whereby to automatically position said detector substantially adjacent to said second anatomical site when said stimulator is placed substantially adjacent to said first anatomical site, whereby said electrodes are located at proximate points along said second anatomical site;
(b) placing said sensor on an individual so that said stimulator is located superficially at said first anatomical site and said detector is located superficially at said second anatomical site;
(c) operating said stimulator to stimulate said first anatomical site and monitoring said plurality of electrodes to detect response signals produced at said second anatomical site in response to the stimulation at said first anatomical site;
(d) processing the response signals detected by said electrodes, said processing involving an evaluation of two or more selected nerve conduction parameters of each of said response signals and a comparison of said response signals according to the evaluated selected parameters;
(e) selecting on the basis of said comparison of said selected nerve conduction parameters of said response signals processed in step (d) at least one electrode detecting an optimal response signal characteristic of said second anatomical site; and
(f) performing nerve conduction studies according to step (c) with said at least one electrode selected in step (e), said nerve conduction studies comprising stimulating said first anatomical site a plurality of times to evoke response signals at said second site, and then processing said evoked response signals to measure one or more of the following parameters of said evoked response signals: distal motor latency, distal sensory latency, nerve action potential, nerve impulse velocity, amplitude, compound action potential (CMAP) amplitude, F-wave amplitude, F-wave latency, and stimulation threshold.

33. The method of claim 32 wherein time domain features of the response signals are utilized in steps (d) and (e) to determine said at least one electrode.

* * * * *